United States Patent [19]

Terasawa

[11] 3,939,415
[45] Feb. 17, 1976

[54] METHOD OF AND DEVICE FOR MEASURING LIFE TIME OF CARRIERS OF SEMICONDUCTOR

[75] Inventor: Yoshio Terasawa, Hitachi, Japan
[73] Assignee: Hitachi, Ltd., Japan
[22] Filed: July 24, 1974
[21] Appl. No.: 491,230

[30] Foreign Application Priority Data
July 27, 1973  Japan .............................. 48-84013

[52] U.S. Cl. ........ 324/158 D; 324/58 B; 324/158 R
[51] Int. Cl.² .................. G01R 31/26; G01R 27/06
[58] Field of Search .......... 324/158 D, 158 T, 58 B, 324/158 R

[56] References Cited
UNITED STATES PATENTS

| | | | |
|---|---|---|---|
| 2,859,407 | 11/1958 | Henisch | 324/158 D |
| 3,206,674 | 9/1965 | Thuy et al. | 324/158 D |
| 3,500,204 | 3/1970 | Stromer | 324/58 B |

*Primary Examiner*—Alfred E. Smith
*Assistant Examiner*—Ernest F. Karlsen
*Attorney, Agent, or Firm*—Craig & Antonelli

[57] ABSTRACT

There is disclosed a method of and device for measuring characteristics of a semiconductor by way of a microwave. The variation with time in the concentration of carriers which are produced in the semiconductor by applying an energy thereto from an external energy source such as light source is measured by way of a reflected microwave of an incident microwave directed to a portion of the semiconductor through a tapering antenna, whereby the life time of carriers in the semiconductor is determined.

5 Claims, 8 Drawing Figures

METHOD OF AND DEVICE FOR MEASURING LIFE TIME OF CARRIERS OF SEMICONDUCTOR

BACKGROUND OF THE INVENTION

1. Field of the Invention

This invention relates to measurement of characteristics of a semiconductor, especially of the life time of carriers thereof.

2. Brief Description of the Prior Art

The manufacturing processes of semiconductor elements, for example, power diodes or thyristors include cutting a bar-shaped N-type silicon starting substrate to a desired thickness (for example, of the order of several hundred microns) and diffusing a P-type impurity such as galium into a cut N-type silicon wafer to produce a PNP wafer. However, after such PNP wafers are prepared, the life time of carriers often reduces to below a standard value, thereby providing poor or bad wafers.

For this reason, it is necessary to measure the life time of carriers of PNP wafers for the purpose of picking out poor wafers.

A diode method has generally been used for measuring the life time of carriers. In accordance with the diode method, several sheets of PNP wafers are picked up from several tens of sheets of PNP wafers and one of the P-type layers of a PNP wafer is removed by etching to form a PN junction, that, is a diode. Thereafter, a forward current of square waveform is passed through the diode and the life time of carriers is determined from the variation with time in a voltage drop across the anode and cathode of the diode after the interruption of the forward current. In this method, however, even when only one of the picked-up PNP wafer of semiconductor samples has life time below a standard value, the total number of PNP wafers of that particular lot are condemned and thus an improvement in productivity cannot be expected. This method has further a disadvantage that a destructive measurement of PNP wafers prevents the measurement for total number of samples, resulting in an inaccurate measurement.

A method capable of measuring the characteristics of the total number of samples non-destructively has been proposed wherein a sample is inserted into a microwave-guide and a microwave is utilized for the measurement. In this method, however, measurement of characteristics of semiconductors such as diodes and thyristors is impossible since these semiconductor samples have a thickness of about 200 to 1000 microns and a diameter of about 10 to 50 millimeters. Because of large size, they cannot be inserted into the waveguide.

SUMMARY OF THE INVENTION

A main object of this invention is to provide a method and a device capable of measuring, by way of a microwave, the life time of carriers of all semiconductor samples non-destructively without depending upon the configuration of the semiconductor samples.

Another object of this invention is to provide a method and a device capable of measuring the life time of carriers of a semiconductor sample in a small portion thereof.

A main feature of this invention lies in that a microwave is directed to a small portion of the semiconductor sample through an antenna of a waveguide whose one end portion is tapered and has an opening of a drawing pen shape, the semiconductor sample is applied with an energy from an external energy source and the variation with time in the concentration of carriers produced in the semiconductor sample is measured by way of a reflected microwave of the incident microwave directed to a portion of the semiconductor sample, whereby the life time of carriers of the semiconductor specimen is determined.

Other objects and features of the invention will become apparent from the following description taken in conjunction with the accompanying drawings.

DETAILED DESCRIPTION OF THE PREFERRED EMBODIMENTS

Figure 1:
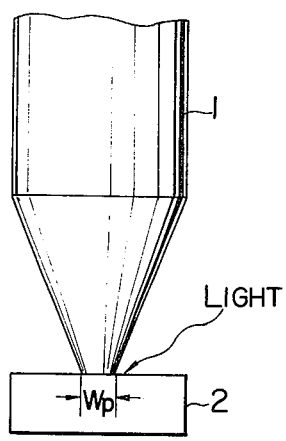
FIGS. 1 and 2 are diagramatic representations for explaining a basic principle of the invention, FIG. 1 being a front view and FIG. 2 being a side view.
Figure 2:
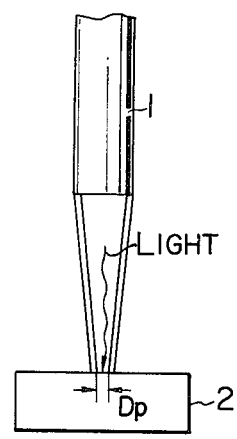

FIGS. 1 and 2 are to show the basic principle of the invention. In the figures, reference numeral 1 designates an antenna of, for example, a rectangular waveguide of $TE_{10}$ mode, whose side walls parallel to the waveguide are tapered at their one-ends to terminate with a width $W_p$ as shown in FIG. 1, a distance between the opposed side walls being gradually narrowed toward their ends to take the shape of a "drawing pen" which has an opening of a gap $D_p$ as shown in FIG. 2. Numeral 2 designates a semiconductor sample to be measured. The end of the antenna 1 is positioned upon the surface of the semiconductor sample 2.

The effective area to be measured by the antenna 1 was determined by comparing the detected voltages of the reflected microwaves between two cases when either the surface of the semiconductor sample was covered or not by a metal sheet with a hole having the same area as the opening of the antenna end. The area of this opening is $W_p \times D_p$ as denoted in FIGS. 1 and 2. The antenna was constructed in such a way that the difference between the detected voltages of the deflected microwaves in those two cases was smaller than ten percents. The experiments show that the effective area to be measured can be minimized to approximately $W_p \times D_p = 0.01$ to $0.1$ mm$^2$.

Figure 3:
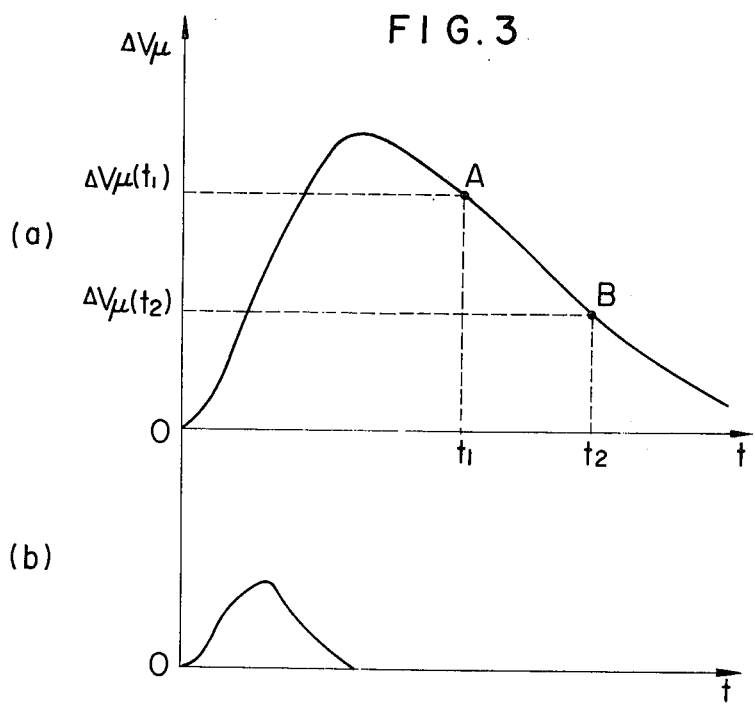
FIG. 3 is a waveform diagram to show the principle of the invention.

In measuring the life time of carriers of the semiconductor sample 2, a light pulse as shown in (b) of FIG. 3 or of a square waveform is directed to semiconductor sample 2 so as to produce carriers therein.

The life time $\tau$ of carriers of the semiconductor sample 2 is given by the following equation:

$$\tau = - \left[ \frac{d \ln \overline{P(z)}}{dt} \right]^{-1} \quad (1)$$

Here, $\overline{P(z)}$ represents an average value of the concentration of carriers produced by the light irradiation. This shows that the life time $\tau$ of carriers can be determined by measuring the attenuation with time in the concentration of carriers produced by the light irradiation, which attenuation may be caused by recombination of the carriers.

On the other hand, since the variation in a microwave detection voltage $\Delta V\mu$ obtained by detecting a reflected microwave of a microwave incident to the semiconductor sample 2 through the antenna 1 has a relation to the variation in the concentration of carriers produced by the light irradiation, equation (1) can be transformed into the following equation:

$$\tau = - \left[ \frac{1}{a} \cdot \frac{\Delta V\mu (t_2) - \Delta V\mu (t_1)}{t_2 - t_1} \right]^{-1} \quad (2)$$

Here, $a$ represents a constant which is determined by a relation between the concentration of carriers of the semiconductor sample and the variation in the microwave detection voltage.

Accordingly, when the attenuation with time in the concentration of carriers which are produced by directing a light pulse as shown in ($b$) of FIG. 3 to the semiconductor sample 2 is illustrated in terms of the variation with time in the microwave detection voltage, a waveform as shown in ($a$) of FIG. 3 is obtained. By calculating the right term of equation (2) by way of the gradient between points A and B of the waveform shown in ($a$) of FIG. 3, the life time $\tau$ of carriers of the semiconductor sample 2 can be determined.

Figure 4:
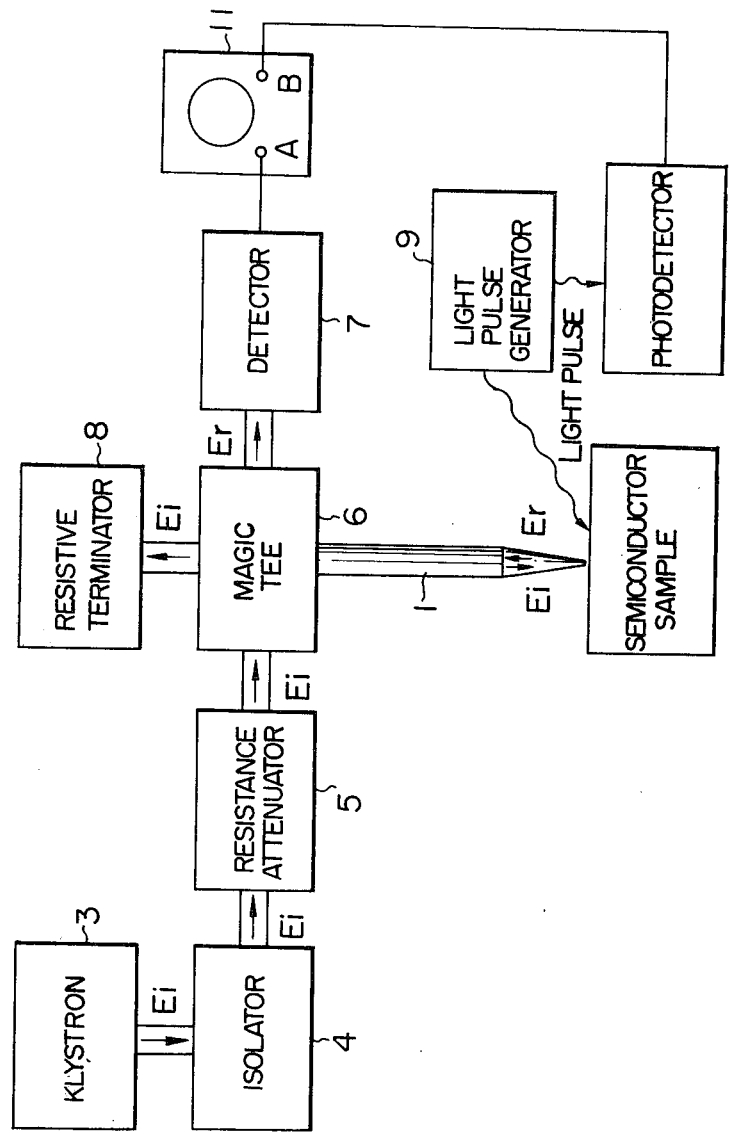
FIG. 4 is a block diagram of a device for measuring the life time of carriers of a semiconductor by way of a microwave embodying the invention.

Reference is now made to FIG. 4 in which like reference numerals show like parts of FIGS. 1 and 2. In FIG. 4, reference numeral 1 designates an antenna, numeral 2 a semiconductor sample, numeral 3 a klystron, numeral 4 an isolator, numeral 5 a resistance attenuator, numeral 6 a magic tee (T), numeral 7 a detector, and numeral 8 a resistive terminator. These components are well known and no description thereof is given. Numeral 9 designates a light pulse generator which irradiates a light pulse as shown in ($b$) of FIG. 3 on the semiconductor sample 2 at the vicinity of a portion thereof to which the end of the antenna 1 engages. The light pulse generator 9 may be a spark gap, xenon lamp, Kerr cell, light emitting diode or the like. Numeral 10 designates a photodetector for detecting the shape of the light pulse emanated from the light pulse generator 9 to the semiconductor sample 2. Numeral 11 designates a synchroscope whose input terminal A is connected to an output side of the detector diode 7 and whose input terminal B is connected to an output side of the photodetector 10. The synchroscope 11 displays on its screen a signal of the microwave detection voltage waveform as shown in ($a$) of FIG. 3 when receiving it at the input terminal A and a signal of the light pulse waveform as shown in ($b$) of FIG. 3 when receiving it at the input terminal B, respectively.

The photodetector 10 is unnecessary for measuring the life time of carriers of the semiconductor sample 2 and it may be omitted.

In operation, a microwave Ei generated at the klystron 3 is applied to the magic tee 6 through the isolator 4 and the resistance attenuator 5. The microwave Ei is propagated to the antenna 1 and the resistive terminator 8 by the aid of the magic tee 6. The microwave Ei propagating through the antenna 1 impinges upon the semiconductor sample 2 which engages with a tapering end portion of the antenna 1. A reflected wave Er of the microwave Ei also propagates through the antenna 1 and returns to the magic tee 6. The reflected wave Er is directed by the aid of the magic tee 6 to the detector 7 at which it is detected. On the other hand, a portion of the incident microwave Ei directed to the resistive terminator 8 is naturally attenuated therein.

Thus, by observing the variation with time in a detection voltage of the reflected microwave Er by the synchroscope 11, it is possible to measure the variation with time in the concentration of carriers which are produced in the semiconductor sample 2 by the irradiation of a light pulse emanated from the light pulse generator 9, thereby determining the life time of carriers of the semiconductor sample 2.

Incidentally, in the case where the life time of carriers of a PNP wafer produced by diffusing an impurity such as gallium into a N-type silicon wafer is to be measured in the process of manufacturing such elements as power diodes or thyristors, the measurement can be accomplished by substituting the PNP wafer for the semiconductor sample 2 of FIG. 4. In measurement of the life time of carriers in the N-type layer, if the P-type layer is thick or the resistivity thereof is small, a light pulse and a microwave cannot reach the N-type layer to be measured, with the result that the measurement of the life time of carriers is sometimes prevented.

Figure 5A:
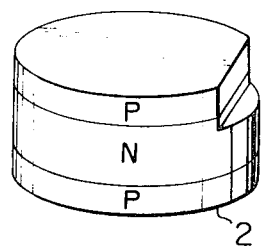
FIGS. 5a and 5b are diagramatic representations of a semiconductor wafer for explaining an application example of the invention.
Figure 5B:
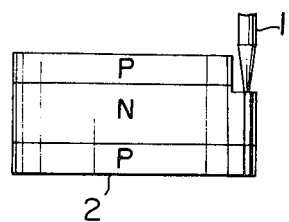

Accordingly, in such a case, a portion of the periphery of the PNP wafer is removed at the P-type layer by etching as shown in FIG. 5$a$ and then at a thus obtained space the tapering end portion of the antenna 1 is engaged with the N-type layer so that a light pulse is irradiated on the N-type layer in order to measure the life time of carriers. It is apparent that this solves the problem mentioned above. Further, it should be understood that the volume of the P-type layer to be removed by etching is needed to be as large as the end portion of the antenna adapted to engage with the N-type layer and it corresponds to a small area of 0.005 to 0.1 mm$^2$ approximately equal to the area of the antenna end. Usually, the peripheral portion of the PNP wafer is removed at the final step for completing an element, and accordingly no adverse effect arises from the removal of a portion or the P-type layer by etching as shown in FIG. 5.

Figure 6:
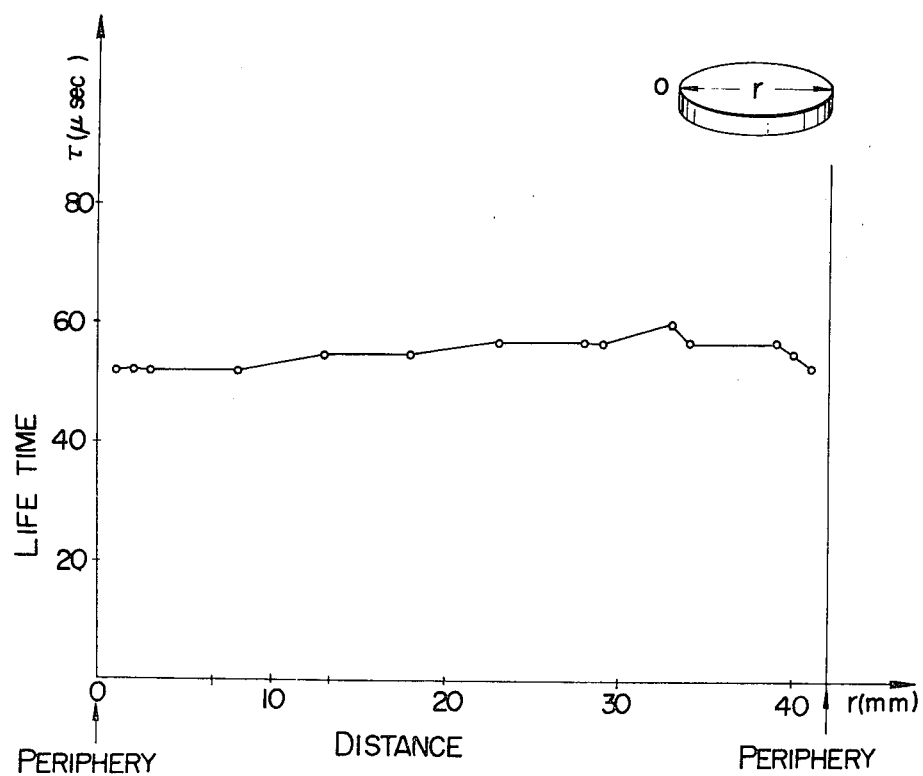
FIGS. 6 and 7 are graphs showing characteristics of semiconductor samples.
Figure 7:
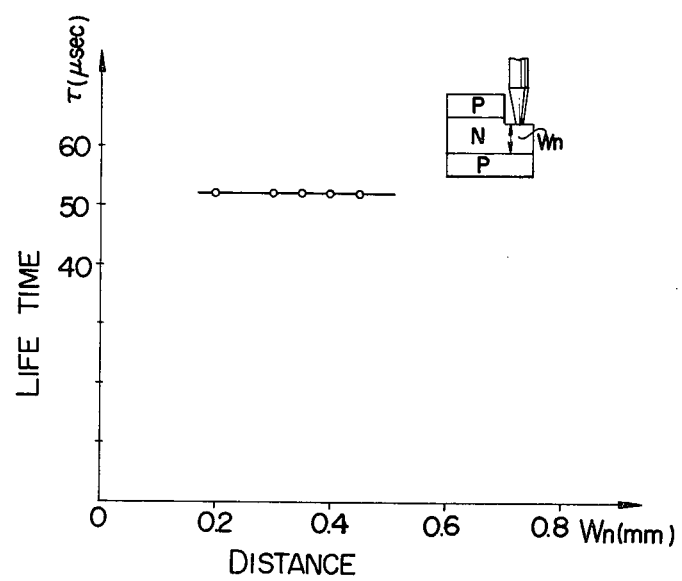

Turning now to FIGS. 6 and 7, the life time characteristics of carriers of the semiconductor sample 2 (PNP wafer) thus obtained will be explained. In FIG. 6, the abscissa represents a radial distance $r$ (mm) starting from the periphery of the semiconductor sample 2 and the ordinate represents life time $\tau(\mu\text{sec.})$. As seen from FIG. 6, the measured values of life time are approximately equal irrespective of the distance $r$. This means, as described in the foregoing, that the life time of carriers can be determined without depending upon positions of the antenna.

Further, as seen from FIG. 7 illustrating a relation between the thickness Wn (mm) of the N-type layer of the semiconductor sample 2 (PNP wafer) and life time $\tau(\mu\text{sec.})$, the life time $\tau$ can be measured irrespective of the thickness Wn of the N-type layer.

It should be understood that the semiconductor sample is not limited to the PNP wafer, but it may be a N-type wafer alone such as a N-type silicon wafer without undergoing diffusion of an impurity such as gallium, P-type wafer, NPN wafer, or NPNP wafer.

Further, while in the foregoing description a light pulse has been used for producing carriers in the semiconductor sample other electromagnetic waves such as X-rays or $\gamma$-rays and beams of particles such as $\alpha$-rays may be used.

As has been described, according to the invention, since a microwave is radiated upon a very small area of the surface of the semiconductor sample through the antenna having a tapering end portion with a drawing pen shaped opening, carriers are produced in the semiconductor sample by energy irradiation from a separate energy source and attenuation with time in the concentration of carriers is measured by way of a reflected microwave of the incident microwave so that the life time of carriers of the semiconductor sample is determined nondestructively irrespective of the configuration of the semiconductor sample in a fashion of total number inspection. This also improves productivity.

I claim:

1. A method of measuring the life time of carriers of a semiconductor, comprising the steps of supplying energy to a sample of a semiconductor to produce carriers therein, directing a microwave signal to a portion of said semiconductor through an antenna to obtain a microwave signal reflected therefrom, said antenna being a waveguide whose one end portion is tapered and has a drawing pen shaped opening, and detecting the reflected microwave signal from said semiconductor portion representative of the variation in the concentration of said carriers with respect to time which variation has a predetermined relationship to the life time of said carriers.

2. A method according to claim 1, wherein said energy is a light pulse.

3. A method according to claim 2, wherein said light pulse is directed to the vicinity of said semiconductor portion.

4. A method according to claim 3, wherein said semiconductor is a PNP wafer in which one end portion of one of two P-type layers of said PNP wafer is removed exposing that portion of the N type layer of said PNP wafer which provides said semiconductor portion.

5. A device for measuring the life time of carriers of a semiconductor, comprising an energy source for supplying energy to a sample of a semiconductor to produce carriers therein, a microwave signal generating means, an antenna of a waveguide whose one end portion is tapered and has a drawing pen shaped opening, a microwave signal from said microwave signal generating means being directed to a portion of said semiconductor through said antenna to obtain a microwave signal reflected therefrom, a detector means for detecting the reflected microwave signal representative of the variation in the concentration of said carriers with respect to time which variation has a predetermined relationship to the life time of said carriers.

* * * * *